US008563252B2

(12) United States Patent
Aharonov et al.

(10) Patent No.: US 8,563,252 B2
(45) Date of Patent: Oct. 22, 2013

(54) METHODS FOR DISTINGUISHING BETWEEN LUNG SQUAMOUS CARCINOMA AND OTHER NON SMALL CELL LUNG CANCERS

(75) Inventors: Ranit Aharonov, Tel Aviv (IL); Nitzan Rosenfeld, Rehovot (IL); Shai Rosenwald, Nes Ziona (IL); Hila Benjamin, Kiryat Uno (IL)

(73) Assignee: Rosetta Genomics Ltd., Rehovot (IL)

( * ) Notice: Subject to any disclaimer, the term of this patent is extended or adjusted under 35 U.S.C. 154(b) by 716 days.

(21) Appl. No.: 12/551,291

(22) Filed: Aug. 31, 2009

(65) Prior Publication Data
US 2010/0047804 A1 Feb. 25, 2010

Related U.S. Application Data

(63) Continuation-in-part of application No. PCT/IL2008/000261, filed on Feb. 28, 2008, which is a continuation-in-part of application No. 11/130,645, filed on May 16, 2005, now Pat. No. 7,709,616, which is a continuation of application No. PCT/US2005/016986, filed on May 14, 2005, and a continuation-in-part of application No. 10/709,572, filed on May 14, 2004, now Pat. No. 7,888,497, and a continuation-in-part of application No. 10/709,577, filed on May 14, 2004, now Pat. No. 7,687,616.

(60) Provisional application No. 60/904,171, filed on Mar. 1, 2007, provisional application No. 61/021,346, filed on Jan. 16, 2008, provisional application No. 60/666,340, filed on Mar. 30, 2005, provisional application No. 60/665,094, filed on Mar. 25, 2005, provisional application No. 60/662,742, filed on Mar. 17, 2005, provisional application No. 60/593,329, filed on Jan. 6, 2005, provisional application No. 60/593,081, filed on Dec. 8, 2004, provisional application No. 60/522,860, filed on Nov. 15, 2004, provisional application No. 60/522,457, filed on Oct. 4, 2004, provisional application No. 60/522,452, filed on Oct. 3, 2004, provisional application No. 60/522,449, filed on Oct. 3, 2004.

(51) Int. Cl.
C12Q 1/68 (2006.01)
(52) U.S. Cl.
USPC ........................................................ 435/6.16
(58) Field of Classification Search
None
See application file for complete search history.

(56) References Cited

U.S. PATENT DOCUMENTS

| 6,506,559 | B1 | 1/2003 | Fire et al. |
| 7,592,441 | B2 * | 9/2009 | Bentwich et al. ............ 536/24.5 |
| 2001/0053519 | A1 | 12/2001 | Fodor et al. |
| 2006/0105360 | A1 | 5/2006 | Croce et al. |

FOREIGN PATENT DOCUMENTS

| DE | WO03029459 | * | 4/2003 |
| WO | WO03029459 | * | 4/2003 |
| WO | WO 2005/078139 A2 | | 8/2005 |
| WO | WO 2007/148235 A2 | | 12/2007 |

OTHER PUBLICATIONS

Endoh et al. (J. Clin. Oncology, 2004, 22(5):811-819).*
Adams et al. (Nature Genetics, 2004, 36(8): p. 867-871).*
Tamakizawa et al. (Cancer Research, 2004, vol. 64, p. 3753-3756).*
The Office Action received in the related U.S. Appl. No. 12/529,221, dated Jan. 6, 2012.
The Office Communication received in the corresponding European Patent Application No. EP 08710261.2, dated Jun. 21, 2010.
Database Geneseq [online] "Human genome derived single exon probe #18136.", database accession No. ACH84941. (XP002489967).
Database Geneseq [online] "Human mir-107 10RNA oligonucleotide, SEQ ID 63.", database accessopm mp/ AEE04335. (XP002489968).
U.S. Appl. No. 12/529,221, filed Sep. 11, 2009, Rosetta Genomics.
The Office Action received in the related U.S. Appl. No. 12/529,221, dated Jun. 21, 2012.
Barad, et al., MicroRNA expression detected by oligonucleotide microarrays: System establishment and expression profiling in human tissues, *Genome Research*, 2004, vol. 14, pp. 2486-2494.
Benner, et al., "Evolution, language and analogy in functional genomics", *TRENDS in Genetics*, 2001, vol. 17, No. 7, pp. 414-418.
Cheung, et al., "Natural variation in human gene expression assessed in lymphovlastoid cells", *Nature Genetics*, 2003, vol. 33, pp. 422-425.
Labourier, et al., "Experimental and Molecular Therapeutics 37: Prognostic and Predictive Markers, Abstract #4202-MicroRNAs as potential diagnostic markers of disease", *Proc Ameri Assoc Can Res*, 2005, vol. 46, Abstract 4202.
Shingara, et al., "An optimized isolation and labeling platform for accurate microRNA expression profiling", *RNA*, 2005, pp. 1461-1470.
The Office Action received in the related U.S. Appl. No. 12/529,221, dated Mar. 8, 2013.
Kirkali, et al., "Bladder Cancer: Epidemiology, Staging and Grading, and Diagnosis", *Urology*, 2005, vol. 66, pp. 4-34.
Puppo, et al., "New Italian guidelines on Bladder Cancer, based on the World Health Organization 2004 classification", *BJU*, 2010, vol. 106, pp. 168-179.

(Continued)

*Primary Examiner* — Stephanie K Mummert
(74) *Attorney, Agent, or Firm* — Foley & Lardner LLP

(57) ABSTRACT

The present invention provides nucleic acid sequences that are used for identification, classification and diagnosis of specific types of nonsmall-cell lung cancers (NSCLC). The nucleic acid sequences can also be used for prognosis evaluation of a subject based on the expression pattern of a biological sample.

11 Claims, 8 Drawing Sheets

(56) References Cited

OTHER PUBLICATIONS

Peltier, et al., "Normalization of microRNA expression levels in quantitative RT-PCR assays: Identification of suitable reference RNA targets in normal an cancerous human solid tissues", *RNA*, 2008, vol. 14, pp. 844-852.

Vandesompele, et al., "Accurate normalization of real-time quantitative RT-PCR data by geometric averaging of multiple internal control genes", *Genome Biology*, 2002, vol. 3, pp. 1-11.

The International Search Report of the corresponding International PCT Application No. PCT/IL2008/000261, dated Sep. 2, 2008. (15 pgs.).

Database Geneseq [online] "Human genome derived single exon probe #18136.", database accession No. ACH84941. (XP002489967), Jan. 26, 2006.

Database Geneseq [online] "Human mir-107 10RNA oligonucleotide, SEQ ID 63.", database accessopm mp/ AEE04335. (XP02489968), Jul. 29, 2004.

Griffith-Jones, et al., "miRBase: microRNA sequences, targets and gene nomenclature", *Nucleic Acids Research*, vol. 34, 2006, pp. D140-D144.

Jiang, et al., "Real-time expression profiling of microRNA precursors in human cancer cell lines.", *Nucleic Acids Research*, vol. 33, No. 17, 2005, pp. 5394-5403.

Paul, Cynthia, P., "Subcellular distribution of small interfering RNA: directed delivery through RNA polymerase III expression cassettes and localization by in situ hybridization", *Methods in Enzymology*, vol. 392, 2005, pp. 125-145. (XP009103657).

Takamizawa, et al., "Reduced expression of the let-7 microRNAs in human lung cancers in association with shortened postoperative survival", Cancer Research, vol. 64, 2004, pp. 3753-3756.

Thomson, et al., "A custom microarray platform for analysis of microRNA gene expression", *Nature Methods*, vol. 1, No. 1, 2004, pp. 1-7.

Yanaihara, et al., "Unique microRNA molecular profiles in lung cancer diagnosis and prognosis", *Cancer Cell*, vol. 9, No. 3, 2006, pp. 189-198.

\* cited by examiner

Figure 3

| real \ Tag | Adeno | Squamous |
|---|---|---|
| Adeno | 16 | 3 |
| Squamous | 0 | 9 |

Figure 8

| real \ Tag | Adeno | Large cell |
|---|---|---|
| Adeno | 18 | 1 |
| Large cell | 1 | 6 |

SEQUENCE LISTING

<160> NUMBER OF SEQ ID NOS: 30

<210> SEQ ID NO 1
<211> LENGTH: 22
<212> TYPE: RNA
<213> ORGANISM: Homo sapiens

<400> SEQUENCE: 1
uccuucauuc caccggaguc ug                                           22

<210> SEQ ID NO 2
<211> LENGTH: 22
<212> TYPE: RNA
<213> ORGANISM: Homo sapiens

<400> SEQUENCE: 2
uagcuuauca gacugauguu ga                                           22

<210> SEQ ID NO 3
<211> LENGTH: 17
<212> TYPE: RNA
<213> ORGANISM: Homo sapiens

<400> SEQUENCE: 3
gugaagcguu ccauauu                                                 17

<210> SEQ ID NO 4
<211> LENGTH: 110
<212> TYPE: RNA
<213> ORGANISM: Homo sapiens

<400> SEQUENCE: 4
aaagauccuc agacaaucca ugugcuucuc uuguccuuca uuccaccgga gucugucuca    60
uacccaacca gauuucagug gagugaaguu caggaggcau ggagcugaca              110

<210> SEQ ID NO 5
<211> LENGTH: 72
<212> TYPE: RNA
<213> ORGANISM: Homo sapiens

<400> SEQUENCE: 5
ugucggguag cuuaucagac ugauguugac uguugaaucu cauggcaaca ccagucgaug    60
ggcugucuga ca                                                      72

<210> SEQ ID NO 6
<211> LENGTH: 44
<212> TYPE: DNA
<213> ORGANISM: Artificial sequence
<220> FEATURE:
<223> OTHER INFORMATION: Synthetic

<400> SEQUENCE: 6
gcgagcacag aattaatacg actcactatc ggttttttt tttt                     44

<210> SEQ ID NO 7
<211> LENGTH: 28
<212> TYPE: DNA
<213> ORGANISM: Artificial sequence
<220> FEATURE:
<223> OTHER INFORMATION: Synthetic

<400> SEQUENCE: 7

```
cagtcatttg ggtccttcat tccaccgg                                          28
```

<210> SEQ ID NO 8
<211> LENGTH: 28
<212> TYPE: DNA
<213> ORGANISM: Artificial sequence
<220> FEATURE:
<223> OTHER INFORMATION: Synthetic

<400> SEQUENCE: 8

```
cagtcatttg ggtagcttat cagactga                                          28
```

<210> SEQ ID NO 9
<211> LENGTH: 21
<212> TYPE: DNA
<213> ORGANISM: Artificial sequence
<220> FEATURE:
<223> OTHER INFORMATION: Synthetic

<400> SEQUENCE: 9

```
gcaaggatga cacgcaaatt c                                                 21
```

<210> SEQ ID NO 10
<211> LENGTH: 22
<212> TYPE: DNA
<213> ORGANISM: Artificial sequence
<220> FEATURE:
<223> OTHER INFORMATION: Synthetic

<400> SEQUENCE: 10

```
cgttttttttt ttttcagact cc                                               22
```

<210> SEQ ID NO 11
<211> LENGTH: 23
<212> TYPE: DNA
<213> ORGANISM: Artificial sequence
<220> FEATURE:
<223> OTHER INFORMATION: Synthetic

<400> SEQUENCE: 11

```
ccgttttttt tttttcaaca tca                                               23
```

<210> SEQ ID NO 12
<211> LENGTH: 18
<212> TYPE: DNA
<213> ORGANISM: Artificial sequence
<220> FEATURE:
<223> OTHER INFORMATION: Synthetic

<400> SEQUENCE: 12

```
aatatggaac gcttcacg                                                     18
```

<210> SEQ ID NO 13
<211> LENGTH: 22
<212> TYPE: RNA
<213> ORGANISM: Homo sapiens

<400> SEQUENCE: 13

```
uucacaggga ggugucauuu au                                                22
```

<210> SEQ ID NO 14
<211> LENGTH: 23
<212> TYPE: RNA
<213> ORGANISM: Homo sapiens

<400> SEQUENCE: 14
uauggcacug guagaauuca cug 23

<210> SEQ ID NO 15
<211> LENGTH: 23
<212> TYPE: RNA
<213> ORGANISM: Homo sapiens

<400> SEQUENCE: 15
gugccuacug agcugauauc agu 23

<210> SEQ ID NO 16
<211> LENGTH: 23
<212> TYPE: RNA
<213> ORGANISM: Homo sapiens

<400> SEQUENCE: 16
agcagcauug uacagggcua uga 23

<210> SEQ ID NO 17
<211> LENGTH: 21
<212> TYPE: RNA
<213> ORGANISM: Homo sapiens

<400> SEQUENCE: 17
gaaggcgcuu cccuuuagag c 21

<210> SEQ ID NO 18
<211> LENGTH: 23
<212> TYPE: RNA
<213> ORGANISM: Homo sapiens

<400> SEQUENCE: 18
aggaccugcg ggacaagauu cuu 23

<210> SEQ ID NO 19
<211> LENGTH: 21
<212> TYPE: RNA
<213> ORGANISM: Homo sapiens

<400> SEQUENCE: 19
agugguuuua cccuauggua g 21

<210> SEQ ID NO 20
<211> LENGTH: 22
<212> TYPE: RNA
<213> ORGANISM: Homo sapiens

<400> SEQUENCE: 20
uuuccuaugc auauacuucu uu 22

<210> SEQ ID NO 21
<211> LENGTH: 22
<212> TYPE: RNA
<213> ORGANISM: Homo sapiens

<400> SEQUENCE: 21
uggcagugua uuguuagcug gu 22

<210> SEQ ID NO 22
<211> LENGTH: 129
<212> TYPE: RNA
<213> ORGANISM: Homo sapiens

<400> SEQUENCE: 22

```
gggaugccac auucagccau ucagcguaca gugccuuuca cagggaggug ucauuuaugu    60
gaacuaaaau auaaauuuca ccuuucugag aagggu aaug uacagcaugc acugcauaug  120
uguguccc                                                           129

<210> SEQ ID NO 23
<211> LENGTH: 80
<212> TYPE: RNA
<213> ORGANISM: Homo sapiens

<400> SEQUENCE: 23 cguucugug uauggcacug guagaauuca cugugaacag ucuagucag ugaauuaccg     60 aagggccaua aacagagcag                                               80

<210> SEQ ID NO 24
<211> LENGTH: 68
<212> TYPE: RNA
<213> ORGANISM: Homo sapiens

<400> SEQUENCE: 24
cuccggugcc uacugagcug auaucaguuc ucauuuuaca cacuggcuca guucagcagg   60
aacaggag                                                            68

<210> SEQ ID NO 25
<211> LENGTH: 84
<212> TYPE: RNA
<213> ORGANISM: Homo sapiens

<400> SEQUENCE: 25
ucuuacugcc cucggcuucu uuacagugcu gccuuguugc auauggauca agcagcauug   60
uacagggcua ugaaggcauu gaga                                          84

<210> SEQ ID NO 26
<211> LENGTH: 85
<212> TYPE: RNA
<213> ORGANISM: Homo sapiens

<400> SEQUENCE: 26
cucaagcugu gacucuccag agggaugcac uuucucuuau gugaaaaaaa agaaggcgcu   60
ucccuuuaga gcguuacggu uuggg                                         85

<210> SEQ ID NO 27
<211> LENGTH: 116
<212> TYPE: RNA
<213> ORGANISM: Homo sapiens

<400> SEQUENCE: 27
caacuacagc cacuacuaca ggaccaucga ggaccugcgg gacaagauuc uuggugccac   60
cauugagaac gccaggauug uccugcagau caacaaugcu caacuggcug cagaug      116

<210> SEQ ID NO 28
<211> LENGTH: 118
<212> TYPE: RNA
<213> ORGANISM: Homo sapiens

<400> SEQUENCE: 28
gcgcccugug ugucucuc ucuguguccu gccagugguu uuacccuaug guagguuacg     60
ucaugcuguu cuaccacagg guagaaccac ggacaggaua ccggggcacc cucugcgu    118

<210> SEQ ID NO 29
```

-continued

```
<211> LENGTH: 110
<212> TYPE: RNA
<213> ORGANISM: Homo sapiens

<400> SEQUENCE: 29
cgccucagag ccgcccgccg uuccuuuuuc cuaugcauau acuucuuuga ggaucuggcc        60
uaaagaggua uagggcaugg gaaaacgggg cggucggguc cuccccagcg                 110

<210> SEQ ID NO 30
<211> LENGTH: 116
<212> TYPE: RNA
<213> ORGANISM: Homo sapiens

<400> SEQUENCE: 30
gcucuggaua ccugugugug augagcuggc aguguauugu uagcugguug aauaugugaa       60
uggcaucggc uaacaugcaa cugcugucuu auugcauaua caaugaacau cagagu         116
```

METHODS FOR DISTINGUISHING BETWEEN LUNG SQUAMOUS CARCINOMA AND OTHER NON SMALL CELL LUNG CANCERS

CROSS REFERENCE TO RELATED APPLICATIONS

This application is a Continuation in part of International Patent Application PCT/IL2008/000261, filed Feb. 28, 2008, which claims priority from 60/904,171, filed Mar. 1, 2007 and 61/021,346, filed Jan. 16, 2008 and is a Continuation in Part of 11/130,645, filed May 16, 2005, which is a Continuation of International Patent Application PCT/US2005/16986, filed May 14, 2005, 10/709,572 and 10/709,577, both filed on May 14, 2004, which claims priority from 60/666,340, filed Mar. 30, 2005, 60/665,094, filed Mar. 25, 2005, 60/662,742, filed Mar. 17, 2005, 60/593,081, filed Dec. 8, 2004, 60/522,860, filed Nov. 15, 2004, 60/522,457, filed Oct. 4, 2004, 60/522,452, filed Oct. 3, 2004 and 60/522,449 filed Oct. 3, 2004, the contents of which are incorporated herein by reference.

FIELD OF THE INVENTION

The invention relates in general to microRNA molecules associated with specific types of lung cancers, as well as various nucleic acid molecules relating thereto or derived therefrom.

BACKGROUND OF THE INVENTION

In recent years, microRNAs (miRs) have emerged as an important novel class of regulatory RNA, which have a profound impact on a wide array of biological processes.

These small (typically 18-24 nucleotides long) non-coding RNA molecules can modulate protein expression patterns by promoting RNA degradation, inhibiting mRNA translation, and also affecting gene transcription. miRs play pivotal roles in diverse processes such as development and differentiation, control of cell proliferation, stress response and metabolism. The expression of many miRs was found to be altered in numerous types of human cancer, and in some cases strong evidence has been put forward in support of the conjecture that such alterations may play a causative role in tumor progression. There are currently about 700 known human miRs, and their number probably exceeds 800.

Classification of cancer has typically relied on the grouping of tumors based on histology, cytogenetics, immunohistochemistry, and known biological behavior. The pathologic diagnosis used to classify the tumor taken together with the stage of the cancer is then used to predict prognosis and direct therapy. However, current methods of cancer classification and staging are not completely reliable.

Lung cancer is one of the most common cancers and has become a predominant cause of cancer-related death throughout the world. Scientists strive to explore biomarkers and their possible role in the diagnosis, treatment and prognosis of specific lung cancers.

Making the correct diagnosis and specifically the distinction between lung squamous carcinoma and other Non Small Cell Lung Carcinoma (NSCLC) such as but not limited to lung adenocarcinoma, has practical importance for choice of therapy. Severe or fatal hemorrhage is a black box warning for lung squamous carcinoma patients undergoing bevacizumab (Avastin) therapy. To-date there is no objective standardized test for differentiating squamous from non squamous NSCLC.

The search for biomarkers for the early detection and accurate diagnosis of various NSCLC has met with little success. Much emphasis has been placed on the discovery and characterization of a unique tumor marker. However, no marker has been identified that has adequate sensitivity or specificity to be clinically useful, although a combination of multiple markers has been shown to increase diagnostic accuracy.

There is an unmet need for a reliable method for distinguishing between lung squamous cell carcinoma and other NSCLC.

SUMMARY OF THE INVENTION

The present invention provides specific nucleic acid sequences for use in the identification, classification and diagnosis of specific lung cancers. The nucleic acid sequences can also be used as prognostic markers for prognostic evaluation of a subject based on their expression pattern in a biological sample.

The invention further provides a method of classifying NSCLC, the method comprising: obtaining a biological sample from a subject; measuring the relative abundance in said sample of a nucleic acid sequence selected from the group consisting of SEQ ID NOS: 1-5, 13-30, a fragment thereof or a sequence having at least about 80% identity thereto; and comparing said obtained measurement to a reference number representing abundance of said nucleic acid; whereby the differential expression of said nucleic acid sequence allows the classification of said NSCLC.

According to some embodiments, said biological sample is selected from the group consisting of bodily fluid, a cell line and a tissue sample. According to some embodiments, said tissue is a fresh, frozen, fixed, wax-embedded or formalin fixed paraffin-embedded (FFPE) tissue. According to one embodiment, the tissue sample is a lung sample.

According to some embodiments, said NSCLC is selected from the group consisting of lung squamous cell carcinoma, lung adenocarcinoma and lung undifferentiated large cell carcinoma. According to some embodiments, said lung undifferentiated large cell carcinoma is originated from lung squamous cell carcinoma or from adenocarcinoma.

The invention further provides a method for distinguishing between lung squamous cell carcinoma and other NSCLC, the method comprising: obtaining a biological sample from a subject; determining in said sample an expression level of a nucleic acid sequence selected from the group consisting of SEQ ID NOS: 1-5, a fragment thereof or a sequence having at least 80% identity thereto; whereby a relative abundance of SEQ ID NO: 1 indicates the presence of squamous cell carcinoma.

According to some embodiments, said other NSCLC is lung adenocarcinoma.

According to some embodiments, the method comprises determining the expression levels of at least two nucleic acid sequences. According to some embodiments the method further comprising combining one or more expression ratios. According to some embodiments, the expression levels are determined by a method selected from the group consisting of nucleic acid hybridization, nucleic acid amplification, and a combination thereof. According to some embodiments, the nucleic acid hybridization is performed using a solid-phase nucleic acid biochip array. According to certain embodiments, the nucleic acid hybridization is performed using in situ hybridization. According to other embodiments, the nucleic acid amplification method is real-time PCR (RT-PCR). According to one embodiment, said real-time PCR is quantitative real-time PCR (qRT-PCR).

According to some embodiments, the RT-PCR method comprises forward and reverse primers. According to other embodiments, the forward primer comprises a sequence selected from the group consisting of any one of SEQ ID NOS: 7-9. According to some embodiments, the real-time PCR method further comprises hybridization with a probe.

According to other embodiments, the probe comprises a sequence selected from the group consisting of any one of SEQ ID NOS: 10-12.

The invention further provides a method for distinguishing between lung adenocarcinoma and large cell carcinoma, the method comprising: obtaining a biological sample from a subject; determining in said sample an expression level of one or more nucleic acid sequences selected from the group consisting of SEQ ED NOS: 13-30, a fragment thereof or a sequence having at least 80% identity thereto; whereby a relative abundance of said nucleic acid indicates the presence of large cell carcinoma.

The invention further provides a kit for NSCLC classification, said kit comprises a probe comprising a nucleic acid sequence selected from the group consisting of any one of SEQ ID NOS: 10-12 and sequences having at least about 80% identity thereto. According to other embodiments, the kit further comprises a forward primer comprising a sequence selected from the group consisting of any one of SEQ ID NOS: 7-9. According to some embodiments, the kit further comprises instructions for the use of one or more expression ratios in the diagnosis of a specific NCSLC. According to some embodiments, said kit comprises reagents for performing in situ hybridization analysis.

These and other embodiments of the present invention will become apparent in conjunction with the figures, description and claims that follow.

BRIEF DESCRIPTION OF THE DRAWINGS

FIG. 3 is a table showing the sensitivity and specificity of miR-205 in lung samples originating from squamous cell carcinoma vs. adenocarcinoma. The sensitivity of the squamous cell carcinoma detection is 100% (9/9) and the specificity is 84.2% (16/19).

FIG. 8 is a table showing the signal of hsa-miR-513 in lung samples originating from adenocarcinoma and large cell carcinoma. The signal below threshold is adenocarcinoma. The sensitivity of the adenocarcinoma detection is 94.7% (18/19) and the specificity of the signal is 85.7% (6/7).

DETAILED DESCRIPTION OF THE INVENTION

Figure 1:
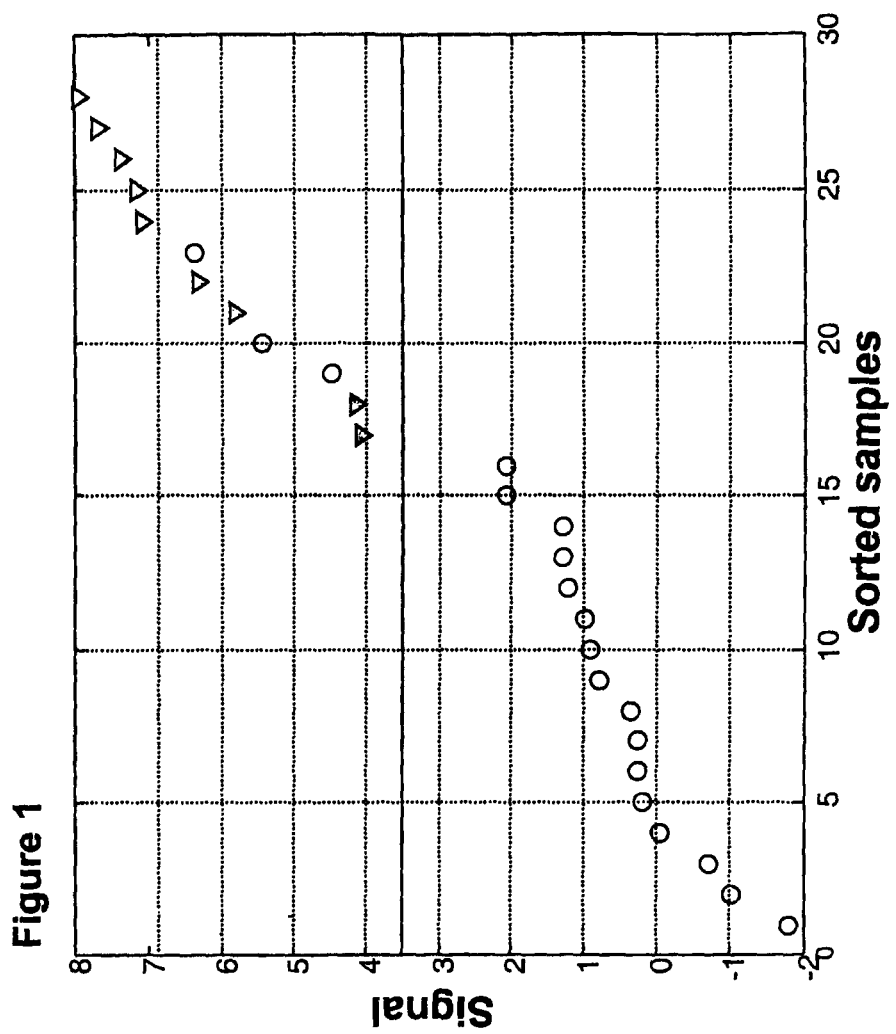
FIG. 1 is a graph showing the normalized expression level, of hsa-miR-205 (SEQ ID NO: 1) based on biochip array, in lung samples originating from adenocarcinoma (circles) or squamous cell carcinoma (triangles). The samples are sorted according to the expression level of hsa-miR-205. X-axis is the sorted samples and y-axis is the normalized expression level. T-test p-value: 9.4735e-007.

The invention is based on the discovery that specific nucleic acid sequences (SEQ ID NOS: 1-5, 13-30) can be used for the identification, classification and diagnosis of specific lung cancers.

The present invention provides a sensitive, specific and accurate method which may be used to distinguish between lung squamous cell carcinoma and other NSCLC.

The methods of the present invention have high sensitivity and specificity. The possibility to distinguish between lung squamous cell carcinoma and other NSCLC such as lung adenocarcinoma or lung large cell carcinoma facilitates providing the patient with the best and most suitable treatment.

Definitions

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9 and 7.0 are explicitly contemplated.

aberrant proliferation

As used herein, the term "aberrant proliferation" means cell proliferation that deviates from the normal, proper, or expected course. For example, aberrant cell proliferation may include inappropriate proliferation of cells whose DNA or other cellular components have become damaged or defective. Aberrant cell proliferation may include cell proliferation whose characteristics are associated with an indication caused by, mediated by, or resulting in inappropriately high levels of cell division, inappropriately low levels of apoptosis, or both. Such indications may be characterized, for example, by single or multiple local abnormal proliferations of cells, groups of cells, or tissue(s), whether cancerous or non-cancerous, benign or malignant.

about

As used herein, the term "about" refers to +/−10%.

antisense

The term "antisense," as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated.

attached

"Attached" or "immobilized" as used herein refer to a probe and a solid support and may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe, or both. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

biological sample

"Biological sample" as used herein means a sample of biological tissue or fluid that comprises nucleic acids. Such samples include, but are not limited to, tissue or fluid isolated from subjects. Biological samples may also include sections of tissues such as biopsy and autopsy samples, FFPE samples, frozen sections taken for histological purposes, blood, plasma, serum, sputum, stool, tears, mucus, hair, and skin. Biological samples also include explants and primary and/or transformed cell cultures derived from animal or patient tissues.

Biological samples may also be blood, a blood fraction, urine, effusions, ascitic fluid, saliva, cerebrospinal fluid, cervical secretions, vaginal secretions, endometrial secretions, gastrointestinal secretions, bronchial secretions, sputum, cell line, tissue sample, or secretions from the breast. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

cancer

The term "cancer" is meant to include all types of cancerous growths or oncogenic processes, metastatic tissues or malignantly transformed cells, tissues, or organs, irrespective of histopathologic type or stage of invasiveness. Examples of cancers include but are nor limited to solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumor, small cell lung, non-small cell lung (e.g., lung squamous cell carcinoma, lung adenocarcinoma and lung undifferentiated large cell carcinoma), oat cell, papillary, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymorna, mesonephroma, myosarcoma, ameloblastoma, cementoma, odontoma, teratoma, thymoma, trophoblastic tumor, adeno-carcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffiii, angiokeratoma, angiolymphoid byperplasia with eosinophilia, angioma sclerosing, angiomatosis, glomangioma, hemangioendothelioma, hemnangioma, hemangiopericytoma, hemnangiosarcoma, lymphangioma, lymphangiomyoma, lymphangiosarcoma, pinealona, carcinosarcoma, chondrosarcoma, cystosarcoma, phyllodes, fibrosarcoma, hemangiosarcoma, leimyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neurofibromatosis, and cervical dysplasia, and other conditions in which cells have become immortalized or transformed.

classification

"Classification" as used herein refers to a procedure and/or algorithm in which individual items are placed into groups or classes based on quantitative information on one or more characteristics inherent in the items (referred to as traits, variables, characters, features, etc) and based on a statistical model and/or a training set of previously labeled items. According to one embodiment, classification means determination of the type of lung cancer.

complement

"Complement" or "complementary" as used herein means Watson-Crick (e.g. A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

Ct

"Ct" as used herein refers to Cycle Threshold of qRT-PCR, which is the fractional cycle number at which the fluorescence crosses the threshold.

detection

"Detection" means detecting the presence of a component in a sample. Detection also means detecting the absence of a component. Detection also means measuring the level of a component, either quantitatively or qualitatively.

differential expression

"Differential expression" means qualitative or quantitative differences in the temporal and/or cellular gene expression patterns within and among cells and tissue. Thus, a differentially expressed gene may qualitatively have its expression altered, including an activation or inactivation, in, e.g., normal versus disease tissue. Genes may be turned on or turned off in a particular state, relative to another state thus permitting comparison of two or more states. A qualitatively regulated gene may exhibit an expression pattern within a state or cell type which may be detectable by standard techniques. Some genes may be expressed in one state or cell type, but not in both. Alternatively, the difference in expression may be quantitative, e.g., in that expression is modulated, either up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, northern analysis, real-time PCR, in situ hybridization and RNase protection.

expression ratio

"Expression ratio" as used herein refers to relative expression levels of two or more nucleic acids as determined by detecting the relative expression levels of the corresponding nucleic acids in a biological sample.

fragment

'Fragment' is used herein to indicate a non-full length part of a nucleic acid or polypeptide. Thus, a fragment is itself also a nucleic acid or polypeptide, respectively.

gene

"Gene" as used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

Groove Binder/Minor Groove Binder (MGB)

"Groove binder" and/or "minor groove binder" may be used interchangeably and refer to small molecules that fit into the minor groove of double-stranded DNA, typically in a sequence-specific manner. Minor groove binders may be long, flat molecules that can adopt a crescent-like shape and thus, fit snugly into the minor groove of a double helix, often displacing water. Minor groove binding molecules may typically comprise several aromatic rings connected by bonds with torsional freedom such as furan, benzene, or pyrrole rings. Minor groove binders may be antibiotics such as netropsin, distamycin, berenil, pentamidine and other aromatic diamidines, Hoechst 33258, SN 6999, aureolic antitumor drugs such as chromomycin and midiramycin, CC-1065, dihydrocyclopyrroloindole tripeptide ($DPI_3$), 1,2-dihydro-(3H)-pyrrolo[3,2-e]indole-7-carboxylate ($CDPI_3$), and related compounds and analogues, including those described in Nucleic Acids in Chemistry and Biology, 2d ed., Blackburn and Gait, eds., Oxford University Press, 1996, and PCT Published Application No. WO 03/078450, the contents of which are incorporated herein by reference. A minor groove binder may be a component of a primer, a probe, a hybridization tag complement, or combinations thereof. Minor groove binders may increase the $T_m$ of the primer or a probe to which they are attached, allowing such primers or probes to effectively hybridize at higher temperatures.

host cell

"Host cell" as used herein may be a naturally occurring cell or a transformed cell that may contain a vector and may support replication of the vector. Host cells may be cultured cells, explants, cells in vivo, and the like. Host cells may be prokaryotic cells such as *E. coli*, or eukaryotic cells such as yeast, insect, amphibian, or mammalian cells, such as CHO and HeLa.

identity

"Identical" or "identity" as used herein in the context of two or more nucleic acids or polypeptide sequences mean that the sequences have a specified percentage of residues that are the same over a specified region. The percentage may be calculated by optimally aligning the two sequences, comparing the two sequences over the specified region, determining the number of positions at which the identical residue Occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

in situ detection

"In situ detection" as used herein means the detection of expression or expression levels in the original site hereby meaning in a tissue sample such as biopsy.

label

"Label" as used herein means a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

nucleic acid

"Nucleic acid" or "oligonucleotide" or "polynucleotide" as used herein mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g. phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005) and Soutschek et al., Nature 432: 173-178 (2004), which are incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver. Mixtures of naturally occurring nucleic acids and analogs may be made; alternatively, mixtures of different nucleic acid analogs, and mixtures of naturally occurring nucleic acids and analogs may be made.

probe

"Probe" as used herein means an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

promoter

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents.

Representative examples of promoters include the bacteriophage T7 promoter, bacteriophage T3 promoter, SP6 promoter, lac operator-promoter, tac promoter, SV40 Late promoter, SV40 early promoter, RSV-LTR promoter, CMV IE promoter, SV40 early promoter or SV40 late promoter and the CMV IE promoter.

selectable marker

"Selectable marker" as used herein means any gene which confers a phenotype on a host cell in which it is expressed to facilitate the identification and/or selection of cells which are transfected or transformed with a genetic construct. Representative examples of selectable markers include the ampicillin-resistance gene ($Amp^r$), tetracycline-resistance gene ($Tc^r$), bacterial kanamycin-resistance gene ($Kan^r$), zeocin resistance gene, the AURI-C gene which confers resistance to the antibiotic aureobasidin A, phosphinothricin-resistance gene, neomycin phosphotransferase gene (nptII), hygromycin-resistance gene, beta-glucuronidase (GUS) gene, chloramphenicol acetyltransferase (CAT) gene, green fluorescent protein (GFP)-encoding gene and luciferase gene.

stringent hybridization conditions

"Stringent hybridization conditions" as used herein mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium).

Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

substantially complementary

"Substantially complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

substantially identical

"Substantially identical" as used herein means that a first and a second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

subject

As used herein, the term "subject" refers to a mammal, including both human and other mammals. The methods of the present invention are preferably applied to human subjects.

target nucleic acid

"Target nucleic acid" as used herein means a nucleic acid or variant thereof that may be bound by another nucleic acid. A target nucleic acid may be a DNA sequence. The target nucleic acid may be RNA. The target nucleic acid may comprise a mRNA, tRNA, shRNA, siRNA or Piwi-interacting RNA, or a pri-miRNA, pTe-miRNA, miRNA, or anti-miRNA.

The target nucleic acid may comprise a target miRNA binding site or a variant thereof. One or more probes may bind the target nucleic acid. The target binding site may comprise 5-100 or 10-60 nucleotides. The target binding site may comprise a total of 5, 6, 7, 8, 9, 10, 11, 12, 13, 14, 15, 16, 17, 18, 19, 20, 21, 22, 23, 24, 25, 26, 27, 28, 29, 30-40, 40-50, 50-60, 61, 62 or 63 nucleotides. The target site sequence may comprise at least 5 nucleotides of the sequence of a target miRNA binding site disclosed in U.S. patent application Ser. Nos. 11/384,049, 11/418,870 or 11/429,720, the contents of which are incorporated herein.

tissue sample

As used herein, a tissue sample is tissue obtained from a tissue biopsy using methods well known to those of ordinary skill in the related medical arts. The phrase "suspected of being cancerous" as used herein means a cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

variant

"Variant" as used herein referring to a nucleic acid means (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

vector

"Vector" as used herein means a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

wild type

As used herein, the term "wild type" sequence refers to a coding, a non-coding or an interface sequence which is an allelic form of sequence that performs the natural or normal function for that sequence. Wild type sequences include multiple allelic forms of a cognate sequence, for example, multiple alleles of a wild type sequence may encode silent or conservative changes to the protein sequence that a coding sequence encodes.

The present invention employs miRNA for the identification, classification and diagnosis of specific lung cancers.

MicroRNA Processing

A gene coding for a microRNA (miRNA) may be transcribed leading to production of an miRNA precursor known as the pri-miRNA. The pri-miRNA may be part of a polycistronic RNA comprising multiple pri-miRNAs. The pri-miRNA may form a hairpin structure with a stem and loop. The stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 60-70 nucleotide precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of the stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. mRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repression or activation), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-7 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have studied the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 Genes Dev 2004-504). However, other parts of the microRNA may also participate in mRNA binding. Moreover, sufficient base pairing at the 3' can compensate for insufficient pairing at the 5' (Brennecke et al, 2005 PLoS 3-e85).

Computation studies, analyzing miRNA binding on whole genomes have suggested a specific role for bases 2-7 at the 5' of the miRNA in target binding but the role of the first nucleotide, found usually to be "A" was also recognized (Lewis et al 2005 Cell 120-15). Similarly, nucleotides 1-7 or 2-8 were used to identify and validate targets by Krek et al (2005, Nat Genet. 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and the binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

Nucleic Acids

Nucleic acids are provided herein. The nucleic acids comprise the sequence of SEQ ID NOS: 1-30 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

Nucleic Acid Complexes

The nucleic acid may further comprise one or more of the following: a peptide, a protein, a RNA-DNA hybrid, an antibody, an antibody fragment, a Fab fragment, and an aptamer.

Pri-miRNA

The nucleic acid may comprise a sequence of a pri-miRNA or a variant thereof. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof. The sequence of the pri-miRNA may comprise the sequence of SEQ ID NOS: 1-2, 4-5, 13-30 or variants thereof.

The pri-miRNA may form a hairpin structure. The hairpin may comprise a first and a second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy of less than −25 Kcal/mole, as calculated by the Vienna algorithm, with default parameters as described in Hofacker et al., Monatshefte f. Chemie 125: 167-188 (1994), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

Pre-miRNA

The nucleic acid may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-2, 4-5, 13-30 or variants thereof.

miRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NOS: 1-2, 13-21 or variants thereof.

Anti-miRNA

The nucleic acid may also comprise a sequence of an anti-miRNA capable of blocking the activity of a miRNA or miRNA*, such as by binding to the pri-miRNA, pre-miRNA, miRNA or miRNA* (e.g. antisense or RNA silencing), or by binding to the target binding site. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the anti-miRNA may comprise (a) at least 5 nucleotides that are substantially identical or complimentary to the 5' of a miRNA and at least 5-12 nucleotides that are substantially complimentary to the flanking regions of the target site from the 5' end of the miRNA, or (b) at least 5-12 nucleotides that aye substantially identical or complimentary to the 3' of a miRNA and at least 5 nucleotide that are substantially complimentary to the flanking region of the target site from the 3' end of the miRNA. The sequence of the anti-miRNA may comprise the compliment of SEQ ID NOS: 1-2, 4-5, 13-30 or variants thereof.

Binding Site of Target

The nucleic acid may also comprise a sequence of a target microRNA binding site or a variant thereof. The target site sequence may comprise a total of 5-100 or 10-60 nucleotides. The target site sequence may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62 or 63 nucleotides. The target site sequence may comprise at least 5 nucleotides of the sequence of SEQ ID NOS: 1-2, 4-5 or 13-30.

Synthetic Gene

A synthetic gene is also provided comprising a nucleic acid described herein operably linked to a transcriptional and/or translational regulatory sequence. The synthetic gene may be capable of modifying the expression of a target gene with a binding site for a nucleic acid described herein. Expression of the target gene may be modified in a cell, tissue or organ. The synthetic gene may be synthesized or derived from naturally-occurring genes by standard recombinant techniques. The synthetic gene may also comprise terminators at the 3'-end of the transcriptional unit of the synthetic gene sequence. The synthetic gene may also comprise a selectable marker.

Vector

A vector is also provided comprising a synthetic gene described herein. The vector may be an expression vector. An expression vector may comprise additional elements. For example, the expression vector may have two replication systems allowing it to be maintained in two organisms, e.g., in one host cell for expression and in a second host cell (e.g., bacteria) for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker gene to allow the selection of transformed host cells.

Host Cell

A host cell is also provided comprising a vector, synthetic gene or nucleic acid described herein. The cell may be a bacterial, fungal, plant, insect or animal cell. For example, the host cell line may be DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). Host cell lines may be available from commercial services, the American Tissue Culture Collection or from published literature.

Probes

A probe is provided herein. A probe may comprise a nucleic acid. The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may comprise a nucleic acid of 18-25 nucleotides.

A probe may be capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. A probe may be single stranded or partially single and partially double stranded. The strandedness of the probe is dictated by the structure, composition, and properties of the target sequence. Probes may be directly labeled or indirectly labeled.

Test Probe

The probe may be a test probe. The test probe may comprise a nucleic acid sequence that is complementary to a miRNA, a miRNA*, a pre-miRNA, or a pri-miRNA. The sequence of the test probe may be selected from SEQ ID NOS: 10-12.

Linker Sequences

The probe may further comprise a linker. The linker may be 10-60 nucleotides in length.

The linker may be 20-27 nucleotides in length. The linker may be of sufficient length to allow the probe to be a total length of 45-60 nucleotides. The linker may not be capable of forming a stable secondary structure, or may not be capable of folding on itself, or may not be capable of folding on a non-linker portion of a nucleic acid contained in the probe. The sequence of the linker may not appear in the genome of the animal from which the probe non-linker nucleic acid is derived.

Reverse Transcription

Target sequences of a cDNA may be generated by reverse transcription of the target RNA. Methods for generating cDNA may be reverse transcribing polyadenylated RNA or alternatively, RNA with a ligated adaptor sequence.

Reverse Transcription Using Adaptor Sequence Ligated to RNA

The RNA may be ligated to an adapter sequence prior to reverse transcription. A ligation reaction may be performed by T4 RNA ligase to ligate an adaptor sequence at the 3' end of the RNA. Reverse transcription (RT) reaction may then be performed using a primer comprising a sequence that is complementary to the 3' end of the adaptor sequence.

Reverse Transcription Using Polyadenylated Sequence Ligated to RNA

Polyadenylated RNA may be used in a reverse transcription (RT) reaction using a poly(T) primer comprising a 5' adaptor sequence. The poly(T) sequence may comprise 8, 9, 10, 11, 12, 13, or 14 consecutive thymines. The reverse transcription primer may comprise SEQ ID NO:6.

RT-PCR of RNA

The reverse transcript of the RNA may be amplified by real time PCR, using a specific forward primer comprising at least 15 nucleic acids complementary to the target nucleic acid and a 5' tail sequence; a reverse primer that is complementary to the 3' end of the adaptor sequence; and a probe comprising at least 8 nucleic acids complementary to the target nucleic acid. The probe may be partially complementary to the 5' end of the adaptor sequence.

PCR of Target Nucleic Acids

Methods of amplifying target nucleic acids are described herein. The amplification may be by a method comprising PCR. The first cycles of the PCR reaction may have an annealing temp of 56° C., 57° C., 58° C., 59° C., or 60° C. The first cycles may comprise 1-10 cycles. The remaining cycles of the PCR reaction may be 60° C. The remaining cycles may comprise 2-40 cycles. The annealing temperature may cause the PCR to be more sensitive. The PCR may generate longer products that can serve as higher stringency PCR templates.

Forward Primer

The PCR reaction may comprise a forward primer. The forward primer may comprise 15, 16, 17, 18, 19, 20, or 21 nucleotides identical to the target nucleic acid.

The 3' end of the forward primer may be sensitive to differences in sequence between a target nucleic acid and a sibling nucleic acid.

The forward primer may also comprise a 5' overhanging tail. The 5' tail may increase the melting temperature of the forward primer. The sequence of the 5' tail may comprise a sequence that is non-identical to the genome of the animal from which the target nucleic acid is isolated. The sequence of the 5' tail may also be synthetic. The 5' tail may comprise 8, 9, 10, 11, 12, 13, 14, 15, or 16 nucleotides. The forward primer may comprise SEQ ID NOS: 7-9.

Reverse Primer

The PCR reaction may comprise a reverse primer. The reverse primer may be complementary to a target nucleic acid. The reverse primer may also comprise a sequence complementary to an adaptor sequence. The sequence complementary to an adaptor sequence may comprise 12-24 nucleotides.

Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined locations on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrate materials include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The substrate of the biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker.

The probes may be attached to the solid support by either the 5' terminus, 3' terminus, or via an internal nucleotide.

The probe may also be attached to the solid support non-ovalently. For example, biotinylated oligonucleotides can be made, which may bind to surfaces covalently coated with streptavidin, resulting in attachment. Alternatively, probes may be synthesized on the surface using techniques such as photopolymerization and photolithography.

Diagnostics

A method of diagnosis is also provided. The method comprises detecting a differential expression level of lung cancer-associated nucleic acids in a biological sample. The sample may be derived from a patient. Diagnosis of a cancer state, and its histological type, in a patient may allow for prognosis and selection of therapeutic strategy. Further, the developmental stage of cells may be classified by determining temporarily expressed cancer-associated nucleic acids.

In situ hybridization of labeled probes to tissue arrays may be performed. When comparing the fingerprints between an individual and a standard, the skilled artisan can make a diagnosis, a prognosis, or a prediction based on the findings. It is further understood that the genes which indicate the diagnosis may differ from those which indicate the prognosis and molecular profiling of the condition of the cells may lead to distinctions between responsive or refractory conditions or may be predictive of outcomes.

Kits

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein.

For example, the kit may be used for the amplification, detection, identification or quantification of a target nucleic acid sequence. The kit may comprise a poly(T) primer, a forward primer, a reverse primer, and a probe.

Any of the compositions described herein may be comprised in a kit. In a non-limiting example, reagents for isolating miRNA, labeling miRNA, and/or evaluating a miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, components for in situ hybridization and components for isolating miRNA. Other kits of the invention may include components for making a nucleic acid array comprising miRNA, and thus, may include, for example, a solid support.

The following examples are presented in order to more fully illustrate some embodiments of the invention. They should, in no way be construed, however, as limiting the broad scope of the invention.

EXAMPLES

Example 1

Experimental Procedures 1. miRdicator™ Array Platform

Custom microarrays were produced by printing DNA oligonucleotide probes to 688 miRs (miRNA) [Sanger database, version 9.1 (miRBase: microRNA sequences, targets and gene nomenclature. Griffiths-Jones S, Grocock R J, van Dongen S, Bateman A, Enright A J. NAR, 2006, 34, Database Issue, D140-D144) and additional Rosetta genomics validated and predicted miRs]. Each probe carries up to 22-nucleotide (nt) linker at the 3'end of the miRNA's complement sequence in addition to an amine group used to couple the probes to coated glass slides. 20 µM of each probe were dissolved in 2×SSC+0.0035% SDS and spotted in triplicate on Schott Nexterion® Slide E coated microarray slides using a Genomic Solutions® BioRobotics MicroGrid II according the MicroGrid manufacturer's directions. 64 negative control probes were designed using the sense sequences of different miRNAs. Two groups of positive control probes were designed to hybridize to miRdicator™ array (1) synthetic spikes small RNA were added to the RNA before labeling to verify the labeling efficiency and (2) probes for abundant small RNA [e.g. small nuclear RNAs (U43, U49, U24, Z30, U6, U48, U44), 5.8s and 5s ribosomal RNA] were spotted on the array to verify RNA quality. The slides were blocked in a solution containing 50 mM ethanolamine, 1M Tris (pH 9.0) and 0.1% SDS for 20 min at 50° C., then thoroughly rinsed with water and spun dry.

2. Cy-Dye Labeling of microRNA for miRdicator™ Array

15 µg of total RNA was labeled by ligation of a RNA-linker p-rCrU-Cy-dye (Thomson et al., 2004, Nat Methods 1, 47-53) (Dharmacon) to the 3'-end with Cy3 or Cy5. The labeling reaction contained total RNA, spikes (20-0.1 fmoles), 500 ng RNA-linker-dye, 15% DMSO, 1× ligase buffer and 20 units of T4 RNA ligase (NEB) and proceeded at 4° C. for 1 hr followed by 1 hr at 37° C. The labeled RNA was mixed with 3× hybridization buffer (Ambion), heated to 95° C. for 3 min and then added on top of the miRdicator™ array. Slides were hybridize 12-16 hr, followed by two washes with 1× SSC and 0.2% SDS and a final wash with 0.1× SSC.

The array was scanned using an Agilent Microarray Scanner Bundle G2565BA (resolution of 10 µm at 100% power). The data was analyzed using SpotReader software.

3. RNA Extraction

RNA was extracted from frozen or formalin fixed paraffin-embedded (FFPE) tissues originating from lung adenocarcinoma, lung squamous cell carcinoma and lung large cell carcinoma.

Total RNA from frozen tissues was extracted with the miRvana miRNA isolation kit (Ambion) according to the manufacturer's instructions.

Total RNA from formalin fixed, paraffin-embedded (FTPE) tissues was extracted according to the following protocol:

1 ml Xylene (Biolab) was added to 1-2 mg tissue, incubated at 57° C. for 5 min and centrifuged for 2 min at 10,000 g. The supernatant was removed and 1 ml Ethanol (100%) (Biolab) was added. Following centrifugation for 10 min at 10,000 g, the supernatant was discarded and the washing procedure was repeated. Following air drying for 10-15 min, 500 µl Buffer B (NaCl 10 mM, Tris pH 7.6, 500 mM, EDTA 20 mM, SDS 1%) and 5 µl proteinase K (50 mg/ml) (Sigma) were added. Following incubation at 45° C. for 16 h, inactivation of the proteinase K at 100° C. for 7 min was preformed. Following extraction with acid phenol chloroform (1:1) (Sigma) and centrifugation for 10 min at maximum speed at 4° C., the upper phase was transferred to a new tube with the addition of 3 volumes of 100% Ethanol, 0.1 volume of NaOAc (BioLab) and 8 µl glycogen (Ambion) and left over night at −20° C.

Following centrifugation at maximum speed for 40 min at 4° C., washing with 1 ml Ethanol (85%), and drying, the RNA was re-suspended in 45 µl DDW.

The RNA concentration was tested and DNase Turbo (Ambion) was added accordingly (1 µl DNase/10 µg RNA). Following Incubation for 30 min at room temperature and extraction with acid phenol chloroform, the RNA was re-suspended in 45 µl DDW. The RNA concentration was tested again and DNase Turbo (Ambion) was added accordingly (1 µl DNase/10 µg RNA). Following incubation for 30 min at room temperature and extraction with acid phenol chloroform, the RNA was re-suspended in 20 µl DDW.

4. RNA Polyadenylation and Annealing of Poly(T) Adapter

A mixture was prepared according to the following:

| Component | Vol/sample |
| --- | --- |
| PNK buffer (NEB) | 1 µl |
| 25 mM MnCl$_2$ (Sigma) | 1 µl |
| 10 mM ATP (Promega) | 2 µl |
| Poly A polymerase (Takara) | 1 µl |
| Total Vol | 5 µl |

5 µl of the mixture were added to 5 µl of appropriate RNA sample (1 µg) (or to the ultra pure water of the No RNA control). The reaction was incubated for 1 hour at 37° C. Poly(T) adapter (GCGAGCACAGAAATTAATACGACT-CACTATCGGTTTTTTTTTTTVN-SEQ ID NO: 6) mixture was prepared according to the following:

| Component | Vol/sample |
| --- | --- |
| 0.5 µg/µl Poly(T) adapter (IDT) | 1 µl |
| Ultra pure water | 2 µl |
| Total Vol | 3 µl |

3 µl from the Poly(T) adapter mixture and 5 µl from the poly-adenylated RNA or negative control were transferred to PCR tubes. Annealing process was performed by the following annealing program:
STEP 1: 85° C. for 2 min
STEP 2: 70° C. to 25° C.—decrease of 1° C. in each cycle for 20 sec.

5. Reverse Transcription

Reverse Transcription mixture was prepared according to the following:

| Component | Vol/sample |
| --- | --- |
| 5x RT buffer (Invitrogen) | 4 µl |
| Trehalose D 1.7M (Calbiochem, Sigma) | 3 µl |
| 10 mM dNTPs mix (Promega) | 1 µl |
| DTT (0.1 M) (Invitrogen) | 2 µl |
| Total Vol | 10 µl |

1.5 µl Recombinant Rnasin (Promega) and 1 µl superscript II RT (Invitrogen) were added to the above mixture. 12.5 µL of the mix were added to each PCR tube containing the annealed PolyA RNA and to the No RNA control.

The tubes were inserted into a PCR instrument (MJ Research Inc.) and the following program was performed:
STEP 1: 37° C. for 5 min
STEP 2: 45° C. for 5 min
STEP 3: Repeat steps 1-2, 5 times
STEP 4: End the program at 4° C.
The cDNA microtubes were stored at −20° C.

6. Real Time PCR Using MGB Probe

Each cDNA sample was evaluated in triplicate for the following three RNAs: hsa-miR-21 (SEQ ID NO: 2), hsa-miR-205 (SEQ ID NO: 1) and U6 (SEQ ID NO: 3).

A primer-probe mix was prepared. In each tube 10 µM Fwd primer with the same volume of 5 µM of the corresponding MGB probe (ABI) specific for the same RNA were mixed. The sequences of the Fwd primers and MGB probes are indicated in Table 1.

TABLE 1

Sequences of primers and probes

| Name | Fwd (Forward miR specific) primer | SEQ ID NO | TaqMan MGB probe | SEQ ID NO |
|---|---|---|---|---|
| miR-205 | CAGTCATTTGGGTCCTTCATTCCACCGG | 7 | CGTTTTTTTTTTTCAGACTCC | 10 |
| miR-21 | CAGTCATTTGGGTAGCTTATCAGACTGA | 8 | CCGTTTTTTTTTTTCAACATCA | 11 |
| U6 | GCAAGGATGACACGCAAATTC | 9 | AATATGGAACGCTTCACG | 12 |

The cDNA was diluted to a final concentration of 0.5 ng/μl. PCR mixture was prepared according to the following:

| Component | Vol per well |
|---|---|
| 2 X TaqMan Universal PCR (ABI) | 10 μl |
| RT-rev-primer-Race 10 μM (IDT) | 1 μl |
| Ultra pure water | 6 μl |
| Total Vol | 17 μl |

68 μl (for No RNA control and for No cDNA control) or 170 μl of the PCR mix were dispensed into the appropriately labeled microtubes. 10 μl cDNA (0.5 ng/μl) were added into the appropriately labeled microtubes containing the mix. The PCR plates were prepared by dispensing 18 μl from the mix into each well. 2 μl of primer probe mixture were added into each well using a PCR-multi-channel. The plates were loaded in a Real Time-PCR instrument (Applied Biosystems) and the following program was performed:

Stage 1. Reps=1
STEP 1: Hold @ 95.0 for 10 min (MM:SS), Ramp Rate=100
Stage 2 Reps=40
STEP 1: Hold @ 95.0 for 0:15 (MM:SS), Ramp Rate=100
STEP 2: Hold @ 60.0 for 1:00 (MM:SS), Ramp Rate=100
Standard 7500 Mode
Sample Volume (μL): 20.0
Data Collection Stage 2, Step 2

7. miRdicator™ Array Data Normalization

The initial data set consisted of signals measured for multiple probes for every sample. For the analysis, signals were used only for probes that were designed to measure the expression levels of known or validated human microRNAs.

Triplicate spots were combined into one signal by taking the logarithmic mean of the reliable spots. All data was log-transformed and the analysis was performed in log-space. A reference data vector for normalization, R, was calculated by taking the mean expression level for each probe in two representative samples, one from each tumor type, for example: lung squamous cell carcinoma and lung adenocarcinoma.

For each sample k with data vector $S^k$, a 2nd degree polynomial $F^k$ was found so as to provide the best fit between the sample data and the reference data, such that $R=F^k(S^k)$. Remote data points ("outliers") were not used for fitting the polynomials F. For each probe in the sample (element $S_i^k$ in the vector $S^k$), the normalized value (in log-space) $M_i^k$ is calculated from the initial value $S_i^k$ by transforming it with the polynomial function $F^k$, so that $M_i^k=F^k(S_i^k)$. Data is translated back to linear-space by taking the exponent.

8. Statistical Analysis

The purpose of this statistical analysis was to find probes whose normalized signal levels differ significantly between the two compared sample sets. Probes that had normalized signal levels below log2(300) in the two sample sets were not analyzed. For each probe, two groups of normalized signals obtained for two sample sets were compared. The p-value was calculated for each probe, using the statistical un-paired two-sided t-test method. The p-value is the probability for obtaining, by chance, the measured signals or a more extreme difference between the groups, had the two groups of signals come from distributions with equal mean values. microRNAs whose probes had the lowest and most significant t-test p-values were selected. A p-value lower than 0.05 means that the probability that the two groups come from distributions with the same mean is lower than 0.05 or 5%, under the assumption of normal (Gaussian) signal distributions. The two groups of signals are likely to result from distributions with different means, and the relevant microRNA is likely to be differentially expressed between the two sets of samples.

9. In Situ Hybridization Detection of hsa-mir-205

Standard paraffin sections of lung squamous cell carcinoma were mounted on Superfrost plus histological slides (Menzel-Glazer). Before the hybridization slides with sections were kept at 60° C. for 2 hrs.

All incubations at pre- and posthybridization steps were performed at room temperature unless stated otherwise. All solutions were prepared using ultrapure water purified by an EASYpure II system (Barnstead) equipped with ultrafilter.

A. Prehybridization Treatment

Sections were deparaffinized by three consecutive incubations in xylene (5 min each) and rehydrated through the following series of ethanols: 100%—3 changes 2 min each, 95% and 70%—2 min each. Then slides were washed for 5 min in ultrapure water, put into 0.01M citrate buffer (pH 6.0) and heated in a water bath until boiling and kept at boiling temperature for 10 min. Then slides were left in the buffer to cool down for 1 hr at room temperature.

Slides were incubated in proteinase K solution (20 μg/ml in 1 mM EDTA/10 mM Tris-HCl pH7.5) for 10 min at 37° C. and immediately fixed in freshly prepared 10% formalin solution in phosphate buffered saline (PBS) for 20 min. Formalin fixation was followed by 5 min incubation in 0.2% glycine in PBS and three 2 min washes in ultrapure water.

Then slides were acetylated by shaking in 1.1% (v/v) solution of triethanolamine to which 0.25% (v/v) of acetic anhydride was added simultaneously with slides. After 5 min a new portion of acetic anhydride was added and acetylation proceeded for another 5 min.

Acetylation was followed by three 2 min washings in ultrapute water and then slides were rapidly dehydrated through graded ethanols (70%, 95%, 100%—2 min each) and air-dried.

B. Hybridization

Hybridization solution was prepared by dilution of digoxigenin labeled LNA enhanced probe complementary to hsa-miR-205 (Exiqon product# 18099-01) diluted to 25 nM in hybridization buffer and ~50 gi of this solution were applied to air-dried sections. For the negative control parallel sections were incubated with control hybridization solution prepared by dilution of digoxigenin labeled scramble-miR LNA probe (Exiqon product# 99001-01).

After application of hybridization solution sections were covered with pieces of polyethylene film cut to the size of sections and incubated overnight at 50° C.

Composition of Hybridization Buffer:

| | |
|---|---|
| Dextran sulfate | 10% |
| SSC | x4 |
| Deionized Formamide | 50% |
| Denhardt's Solution | x1 |
| Salmon sperm DNA | 0.5 mg/ml |
| Yeast tRNA | 0.25 mg/ml |

C. Posthybridization Washing and Immunodetection

After hybridization slides were transferred into 5×SSC preheated to 50° C. and incubated for 30 min. During this incubation covers floated off the slides. Then slides were washed for another 30 min in 2×SSC at 50° C.

Then slides were briefly washed in Tris buffered saline with Tween-20 (TBST—0.15M NaCl, 0.05M Tris-HCl pH 7.5, 0.1% Tween-20) and incubated for 1 hr in blocking solution (10% bovine serum albumin in TBST).

For the detection of bound digoxigenin sections were incubated for 2 brs with sheep anti-digoxigenin antibodies Fab conjugated to alkaline phosphatase (Roche Cat #11093274910) diluted 1:250 in blocking solution followed by 5 washings in TBST. Then slides were briefly washed in alkaline phosphatase buffer (APB—0.1M Tris-HCl pH 9.5, 0.05M NaCl, 0.025M $MgCl_2$) and incubated for 5 hrs in staining solution—APB containing 4.5 µl/ml of 5-bromo-4-chloro-3-indolyl-phosphate (BCIP—stock solution by Roche—Cat#11383221001) and 3.5 µl/ml of 4-Nitro blue tetrazolium chloride (NBT—stock solution by Roche—Cat# 11383213001).

Finally, sections were washed in distilled water and coverslipped using Immu-Mount (Thermo Scientific Cat# 9990402).

Example 2

Specific microRNAs are Able to Distinguish Between Lung Adenocarcinoma and Lung Squamous Cell Carcinoma The statistical analysis of the miRdicator™ arrays results of lung adenocarcinoma vs. lung squamous cell carcinoma are presented in Table 2. The results exhibited a significant difference in the expression pattern of hsa-miR-205 (SEQ ID NO 1).

Figure 2:
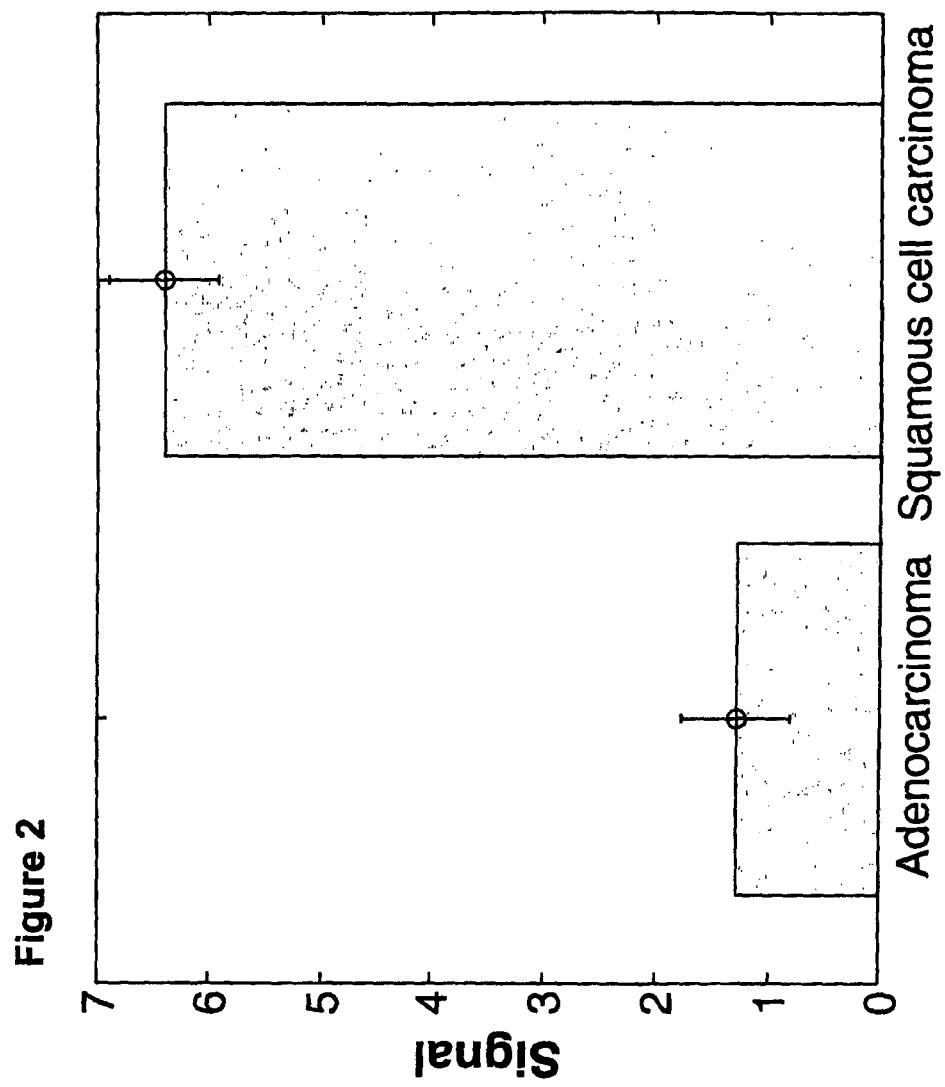
FIG. 2 is a graph showing the average normalized signal and standard error (STD/sqrt(n)) of hsa-miR-205 in two lung sample sets: adenocarcinoma and squamous cell carcinoma.

The normalized expression levels of hsa-miR-205 were found to increase in lung squamous cell carcinoma in comparison to lung adenocarcinoma, as measured by miRdicator™ array (FIGS. 1-3).

The sensitivity of the squamous cell carcinoma detection by hsa-miR-205 is 100% (919) and the specificity of the signal is 84.2% (16/19).

Example 3

Establishment of qRT-PCR Assay for Distinguishing Between Lung Squamous Cell Carcinoma and Other NSCLC RNA was extracted from 20 lung samples of paraffin-embedded (FFPE) tissues originating from lung squamous cell carcinoma and other Non Small Cell Lung Carcinoma (NSCLC) as described in Example 1 (3). The expression levels of hsa-miR-205 (SEQ ID NO: 1), hsa-miR-21 (SEQ ID NO: 2) and U6 (SEQ ID NO: 3) were detected by quantitative qRT-PCR assay as described in Example 1 (4-6). The weighted Ct of 3 repeats of the 3 probes was calculated. The Ct of negative control wells was underdetermined.

The data was interpreted according to the following criteria:

U6 should have a weighted Ct of between 20 to 32. If not the experiment failed.

The weighted Ct of the 3 repeats was calculated according to the following:

If all repeats were within a difference of 1 Ct, meaning that the difference between the minimal and maximal Cts was less than 1, then their average was calculated.

$$Ct_{max} - Ct_{min} \leq 1 \rightarrow \text{weighted } Ct = (Ct_{max} + Ct_{median} + Ct_{min})/3$$

The average of the outlier Cts were calculated, if they had a difference of 1 Ct or less from the middle Ct value.

$$Ct_{max} - Ct_{median} \leq 1 \text{ \& } Ct_{median} - Ct_{min} \leq 1 \rightarrow \text{weighted } Ct = (Ct_{max} + Ct_{median} + Ct_{min})/3$$

Using the weighted calculated Ct, the assay final score was determined by subtracting the average Cts of U6 and hsa-miR-21 from the Ct of hsa-mir-205.

$$\text{Assay final score} = \text{weighted } Ct_{mir-205} - \text{average}[(\text{weighted } Ct_{mir-21} \text{ \& weighted } Ct_{U6})]$$

If the Ct of hsa-mir-205 was undetermined and the weighted Ct of U6 was within the legitimate range then the assay result is "Non-Squamous" with "High" confidence level.

$$Ct_{mir-205} = ND \text{ \& } 20 \leq Ct_{U6} \leq 32 \rightarrow \text{Assay result} = \text{Non-Squamous with high confidence.}$$

Otherwise: The result analysis is based on the assay final score calculation as described in Table 3:

TABLE 2

| miR name | HID | MID | Mean adenocarcinoma (log) | Mean squamous (log) | Number of samples, adenocarcinoma | Number of samples, squamous | p-value |
|---|---|---|---|---|---|---|---|
| hsa-miR-205 | 4 | 1 | 7.49 | 12.04 | 19 | 9 | 9.47E−07 | miR name: is the miRBase registry name (release 9.1).
HID: is the SEQ ID NO of the microRNA hairpin precursor (Pre-microRNA).
MID: is the SEQ ID NO of the mature microRNA.
Mean adenocarcinoma (log): is the mean of the logarithms (log) of chip signal of lung adenocarcinoma samples.
Mean squamous (log): is the mean of the logarithms (log) of chip signal of lung squamous samples.
Number of samples, adenocarcinoma: is the number of lung adenocarcinoma samples.
Number of samples, squamous: is the number of lung squamous samples.
p-value: is the result of the un-paired two-sided t-test between samples

TABLE 3

| Assay final score | Assay result | Confidence |
|---|---|---|
| ≥4 | Non-Squamous | High |
| ≤1 | Squamous cell carcinoma | High |
| ≥2.5 and <4 | Non-Squamous | Low |
| >1 and <2.5 | Squamous cell carcinoma | Low |

Figure 4:
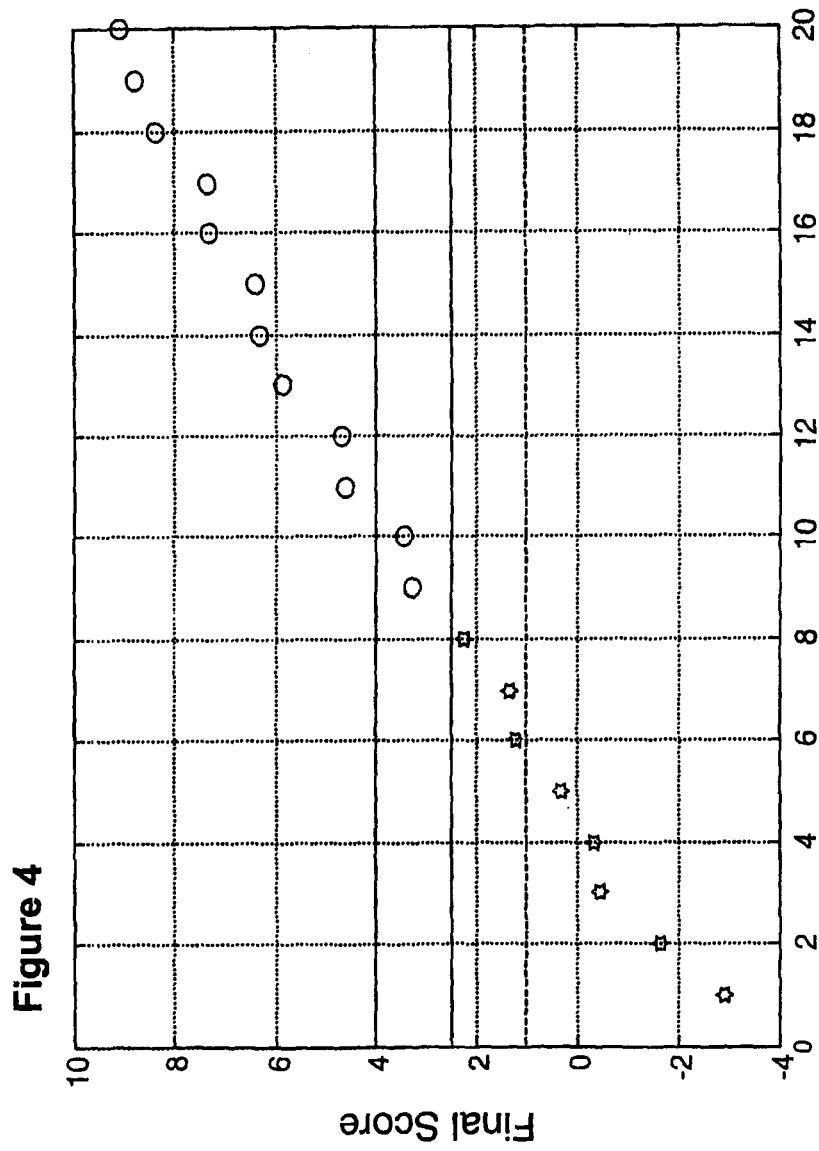
FIG. 4 is a graph showing the full separation between samples originating from lung squamous cell carcinoma (asterisks) and samples originating from other NCSLC (ellipses) using qRT-PCR expression levels of hsa-miR-205 (SEQ ID NO: 1), normalized by qRT-PCR expression levels of hsa-miR-21 (SEQ ID NO: 2), U6 (SEQ ID NO: 3) and a threshold of a final score as described in Example 3. Full black line represents the threshold. Dashed black lines indicate low confidence area border.

FIG. 4 demonstrates the full separation between samples originated from lung squamous cell carcinoma (asterisks) and samples originated from other NSCLC including lung adenocarcinoma and lung undifferentiated large cell carcinoma (ellipses) using RT-PCR expression levels of hsa-miR-205 (SEQ ID NO: 1), normalized by qRT-PCR expression levels of hsa-miR-21 (SEQ ID NO: 2), U6 (SEQ ID NO: 3) and a threshold of a final score as described above. The full black line represents the threshold. The dashed black lines indicate the low confidence area border.

Example 4

In Situ Hybridization Detection of hsa-mir-205

Sections of lung squamous cell carcinoma were hybridized to hsa-miR-205 specific probe and control (scramble) probe (see Example 1).

Figure 5:
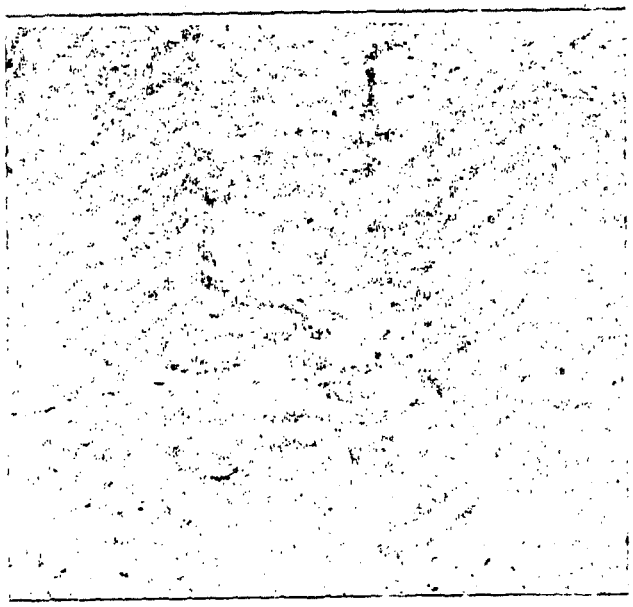
FIG. 5 is a photograph showing in situ hybridization detection of hsa-mir-205. Microphotographs of parallel sections of lung squamous cell carcinoma sections were hybridized to hsa-miR-205 specific probe (A) and control (scrambled) probe (B).

As shown in FIG. 5, staining of varying intensity of cells of squamous cell carcinoma was observed (FIG. 5A) while no staining was detected in sections hybridized to control (scramble) probe (FIG. 5B).

Example 5

Specific microRNAs are Able to Distinguish Between Lung Adenocarcinoma and Lung Large Cell Carcinoma The statistical analysis of the miRdicator™ arrays results of lung adenocarcinoma vs. lung large cell carcinoma are presented in Table 4. The results exhibited a significant difference in the expression pattern of several miRs, most prominent among them being hsa-miR-513 (SEQ ID NO: 13).

Figure 6:
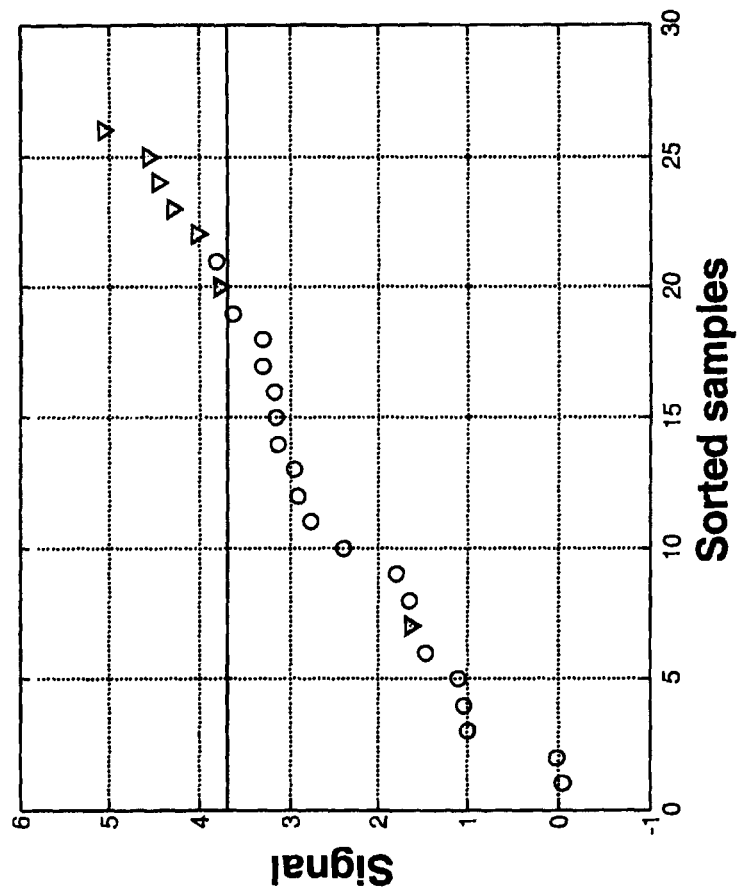
FIG. 6 is a graph showing the normalized expression level of hsa-miR-513 (SEQ ID NO: 13) in lung samples originating from adenocarcinoma (circles) or large cell carcinoma (triangles). The samples are sorted according to hsa-miR-513 expression level. X-axis is the sorted samples and y-axis is the normalized expression level. T-test p-value: 6.1444e-005.
Figure 7:
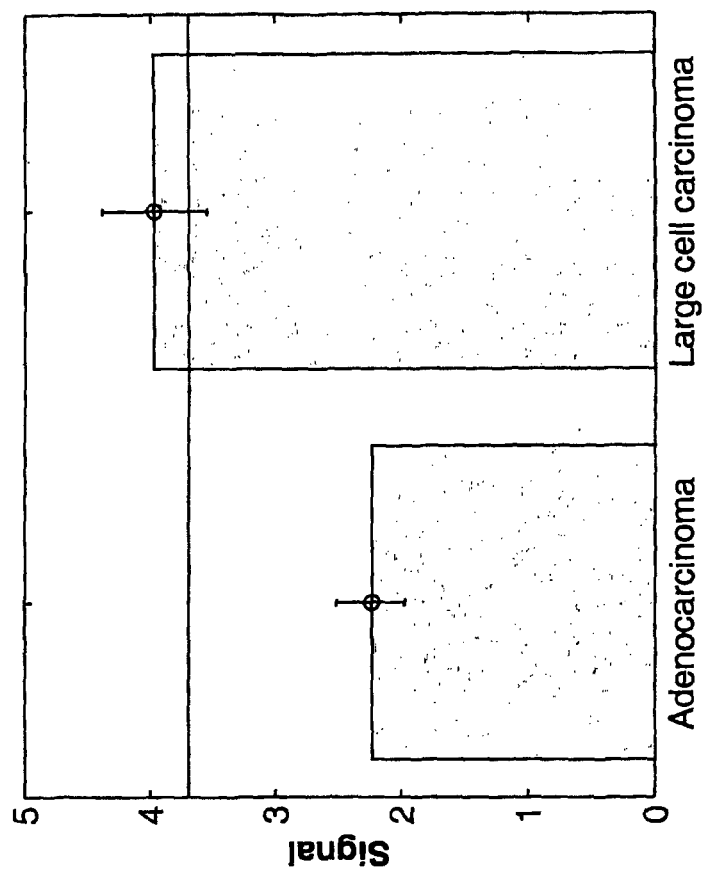
FIG. 7 is a graph showing the average normalized signal and standard error (STD/sqrt(n)) of hsa miR-513 in the two lung sample sets: adenocarcinoma and large cell carcinoma.

The normalized expression levels of hsa-miR-513 were found to increase in lung large cell carcinoma in comparison to lung adenocarcinoma, as measured by miRdicator™ array (FIGS. 6-8).

The sensitivity of the adenocarcinoma detection by hsa-miR-513 is 94.7% (18/19) and the specificity of the signal is 85.7% (6/7).

TABLE 4

| miR name | HID | MID | Mean adenocarcinoma (log) | Mean large cell (log) | Number of samples, adenocarcinoma | Number of samples, large cell | p-value |
|---|---|---|---|---|---|---|---|
| hsa-miR-513 | 22 | 13 | 8.27 | 10.31 | 19 | 7 | 6.14E−05 |
| hsa-miR-183 | 23 | 14 | 8.21 | 10.47 | 19 | 7 | 1.71E−04 |
| hsa-miR-189 | 24 | 15 | 7.03 | 8.5 | 19 | 7 | 4.08E−04 |
| hsa-miR-103 | 25 | 16 | 10.39 | 8.59 | 19 | 7 | 4.55E−04 |
| hsa-miR-525* | 26 | 17 | 6.5 | 8.45 | 19 | 7 | 4.72E−04 |
| hsa-miR-492 | 27 | 18 | 7.99 | 9.57 | 19 | 7 | 5.67E−04 |
| hsa-miR-140 | 28 | 19 | 8.02 | 9.49 | 19 | 7 | 9.18E−04 |
| hsa-miR-202* | 29 | 20 | 7.24 | 8.7 | 19 | 7 | 1.09E−03 |
| hsa-miR-449 | 30 | 21 | 9.37 | 11.55 | 19 | 7 | 1.90E−03 | miR name: is the miRBase registry name (release 9.1).
HID: is the SEQ ID NO of the microRNA hairpin precursor (Pre-microRNA).
MID: is the SEQ ID NO of the mature microRNA.
Mean adeoocarcinoma (log): is the mean of the logarithms (log) of chip signal of Lung adenocarcinoma cells.
Mean large cell (log): is the mean of the logarithms (log) of chip signal of Lung Large cells.
Number of samples, adenocarcinoma cells: is the number of samples of Lung adenocarcinoma cells.
Number of samples, large cells: is the number of samples of Lung Large cells.
p-value: is the result of unmatched t-test between samples.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

The invention claimed is:

1. A method for distinguishing between lung squamous cell carcinoma and other Non Small Cell Lung Carcinoma (NSCLC), the method comprising:
obtaining a lung cancer sample from a subject; determining in said sample an expression level of a nucleic acid sequence of SEQ ID NO: 1; and comparing said expression level to an expression level of a nucleic acid sequence of SEQ ID NO: 1 in a Non Small Cell Lung Carcinoma (NSCLC) sample; whereby increased expression of SEQ ID NO: 1 in the lung cancer sample in comparison to the Non Small Cell Lung Carcinoma (NSCLC) sample indicates the presence of squamous cell carcinoma.

2. The method of claim 1, wherein said other Non Small Cell Lung Carcinoma (NSCLC) is lung adenocarcinoma.

3. The method of claim 1, wherein the method comprises determining the expression levels of at least two nucleic acid sequences.

4. The method of claim 1, wherein the method further comprises combining one or more expression ratios of said nucleic acid sequences.

5. The method of claim 1, wherein the expression levels are determined by a method selected from the group consisting of nucleic acid hybridization, nucleic acid amplification, and a combination thereof.

6. The method of claim 5, wherein the nucleic acid hybridization is performed using a solid-phase nucleic acid biochip array or in situ hybridization.

7. The method of claim 5 where n the nucleic acid amplification method is real-time PCR.

8. The method of claim 7, wherein the real-time PCR method comprises forward and reverse primers.

9. The method of claim 8, wherein the forward primer comprises a sequence selected from the group consisting of any one of SEQ ID NOS: 7-9.

10. The method of claim 8, wherein the real-time PCR method further comprises a probe.

11. The method of claim 10, wherein the probe comprises a sequence selected. from the group consisting of any one of SEQ ID NOS: 10-12.

* * * * *

UNITED STATES PATENT AND TRADEMARK OFFICE
CERTIFICATE OF CORRECTION

| | | |
|---|---|---|
| PATENT NO. | : 8,563,252 B2 | Page 1 of 2 |
| APPLICATION NO. | : 12/551291 | |
| DATED | : October 22, 2013 | |
| INVENTOR(S) | : Ranit Aharonov et al. | |

It is certified that error appears in the above-identified patent and that said Letters Patent is hereby corrected as shown below:

In the Specification

Column 3, Line 15,  change "SEQ ED" to --SEQ ID--.

Column 3, Line 28,  change "NCSLC" to --NSCLC--.

Column 3, Line 54,  change "NCSLC" to --NSCLC--.

Column 5, Line 66,  change "mesenchymorna" to --mesenchymoma--.

Column 6, Line 11,  change "nonchromaffiii" to --non-chromaffin--.

Column 6, Line 12,  change "byperplasia" to --hyperplasia--.

Column 6, Line 14,  change "hemnangioma" to --hemangioma--.

Column 6, Line 15,  change "hemnangiosarcoma" to --hemangiosarcoma--.

Column 8, Line 1,  change "Occurs" to --occurs--.

Column 12, Line 37,  change "in to" to --into--.

Column 14, Line 6,  change "complimentary" to --complementary--.

Column 14, Line 52,  change "complimentary" to --complementary--.

Column 14, Line 54,  change "complimentary" to --complementary--.

Column 14, Line 56,  change "aye" to --are--.

Column 14, Line 56,  change "complimentary" to --complementary--.

Column 14, Line 58,  change "complimentary" to --complementary--.

Signed and Sealed this
Ninth Day of September, 2014

Michelle K. Lee
*Deputy Director of the United States Patent and Trademark Office*

CERTIFICATE OF CORRECTION (continued)
U.S. Pat. No. 8,563,252 B2

In the Specification

Column 14, Line 60,   change "compliment" to --complement--.

Column 17, Line 56,   change "ovalently" to --covalently--.

Column 19, Line 36,   change "FTPE" to --FFPE--.

Column 20, Line 1,    change "Adapter" to --Adaptor--.

Column 20, Line 16,   change "adapter" to --adaptor--.

Column 20, Line 23,   change "adapter" to --adaptor--.

Column 20, Line 28,   change "adapter" to --adaptor--.